US00PP22702P2

(12) United States Plant Patent
Smith

(10) Patent No.: US PP22,702 P2
(45) Date of Patent: May 1, 2012

(54) ***ASTER* PLANT NAMED 'SYNPIN HENFIRST'**

(50) Latin Name: *Aster hybrida*
Varietal Denomination: Synpin Henfirst

(75) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 17 days.

(21) Appl. No.: 12/925,666

(22) Filed: Oct. 27, 2010

(51) Int. Cl.
*A01H 5/00* (2006.01)

(52) U.S. Cl. ..... Plt./355

(58) Field of Classification Search ..... Plt./355
See application file for complete search history.

*Primary Examiner* — June Hwu
(74) *Attorney, Agent, or Firm* — Joshua L. Price

(57) ABSTRACT

A new *Aster* plant named 'Synpin Henfirst' particularly distinguished by the medium sized, long lasting, double-type inflorescences with purple-violet ray floret color, dark yellow-green foliage, upright, freely branched and rounded plant habit, and a natural season flowering in early September.

1 Drawing Sheet

Latin name of the genus and species of the plant claimed: *Aster hybrida.*

Varietal denomination: 'Synpin Henfirst'.

BACKGROUND OF THE NEW PLANT

The present invention comprises a new *Aster*, botanically known as *Aster hybrida*, and hereinafter referred to by the variety name 'Synpin Henfirst'.

'Synpin Henfirst' is a product of a planned breeding program. The new cultivar has medium sized, long lasting, double-type inflorescences with purple-violet ray floret color, dark yellow-green foliage, upright, freely branched and rounded plant habit, and a natural season flowering in early-September.

'Synpin Henfirst' originates as a natural whole plant mutation of 'Synhen Thefirst', U.S. Ser. No. 12/925,435, and was discovered and selected by the inventor as a single flowering plant within a large population of the parent cultivar, grown massed in pots outdoors in a controlled breeding program in Alva, Fla. in April 2008. The parent cultivar 'Synhen Thefirst' has a lighter colored ray floret, little lighter green foliage, and slightly larger inflorescences than 'Synpin Henfirst'.

The first act of asexual reproduction of 'Synpin Henfirst' was accomplished when vegetative cuttings were propagated from the initial selection in June 2008 in a controlled environment in Alva, Fla.

BRIEF SUMMARY OF INVENTION

Horticultural examination of plants grown from cuttings of the plant initiated in June 2008, and continuing thereafter, has demonstrated that the combination of characteristics as herein disclosed for 'Synpin Henfirst' are firmly fixed and are retained through successive generations of asexual reproduction.

'Synpin Henfirst' has not been observed under all possible environmental conditions. The phenotype may vary significantly with variations in environment such as temperature, light intensity and day length.

A Plant Breeder's Right for this cultivar was applied for in Canada on Oct. 30, 2009 (09-6778). 'Synpin Henfirst' has not been made publicly available more than one year prior to the filing of this application.

The following traits have been repeatedly observed and are determined to be basic characteristics of the new variety. The combination of these characteristics distinguishes this *Aster* as a new and distinct variety.

BRIEF DESCRIPTION OF THE PHOTOGRAPHS

The accompanying photographic drawing shows typical flower and foliage characteristics of 'Synpin Henfirst' with colors being as true as possible with an illustration of this type.

The photographic drawing shows 3 flowering potted plants of the new variety growing within one pot and a close-up of the flowers.

DETAILED BOTANICAL DESCRIPTION

The plant descriptions, measurements and aforementioned photographs were taken in Gilroy, Calif. in May 2010 under natural light. These plants used in the photograph and descriptions were about 12 weeks old. Three plants were grown together in an 8 inch pot.

Color references are made to The Royal Horticultural Society Colour Chart (R.H.S.) 2001.

TABLE 1

DIFFERENCES BETWEEN THE NEW VARIETY 'SYNPIN HENFIRST' AND A SIMILAR VARIETY: 'VICTORIA CELESTE' (U.S. Plant Pat. No.13,333)

| | 'Synpin Henfirst' | 'Victoria Celeste' (U.S. Plant Pat. No. 13,333) |
|---|---|---|
| Foliage length: | Longer | Shorter |
| Phyllary length: | Longer | Shorter |
| Quantity of disc florets: | More | Fewer |
| Natural season flowering response: | 2 weeks earlier | 2 weeks later |

Plant:
*Form, growth and habit*.—Stems upright, freely branching, strong and moderately vigorous growth.
*Plant height*.—About 25 cm.
*Plant height* (*inflorescence included*).—25-30 cm.
*Plant width*.—30-35 cm.
*Garden performance and tolerance to weather*.—Very good.

Roots:
*Number of days to initiate roots*.—10 days at about 22 degrees C.
*Number of days to produce a rooted cutting*.—16-18 days at 22 degrees C.
*Type*.—Fine, fibrous, free branching.
*Color*.—RHS N155B but whiter.

Foliage:
*Arrangement*.—Alternate, simple, sessile.
*Immature, leaf color, upper surface*.—Lighter than RHS 147A.
*Lower surface*.—Between RHS 147A and RHS 147B.
*Mature, leaf color, upper surface*.—RHS 147A.
*Lower surface*.—Between RHS 147A and RHS 147B.
*Length*.—5.3-6.8 cm.
*Width*.—1.2-1.8 cm.
*Shape*.—Broadly ligulate.
*Base shape*.—Cuneate.
*Apex shape*.—Acute.
*Margin*.—Entire.
*Texture, upper surface*.—Mostly glabrous, but pubescent on the margins.
*Lower surface*.—Mostly glabrous, but slightly pubescent on the margins.
*Color of veins, upper surface*.—RHS 144A basally becoming indistinct.
*Color of veins, lower surface*.—RHS 144A basally becoming indistinct.

Stem:
*Quantity of main branches per plant*.—About 3-4.
*Color of stem*.—Closest to RHS 144A.
*Length of stem*.—About 25 cm.
*Diameter*.—0.4 cm.
*Length of internodes*.—0.5-2.0 cm.
*Texture*.—Glabrous; some slight pubescence.
*Color of peduncle*.—Closest to RHS 146A but a little darker.
*Length of peduncle*.—2.0-3.0 cm.
*Peduncle diameter*.—0.15 cm.
*Texture*.—Glabrous; some slight pubescence.

Inflorescence:
*Type*.—Compositae type, solitary inflorescences, borne terminally above foliage, ray florets arranged acropetally on a capitulum.
*Natural season flowering*.—Early September.
*Quantity of inflorescences per plant*.—About 75, plus numerous buds.
*Lastingness of individual blooms on the plant*.—3-4 weeks.
*Fragrance*.—None.

Bud (just when opening/showing color):
*Color*.—RHS 84B with RHS 84A apex.
*Length*.—0.6-0.8 cm.
*Width*.—0.5-0.7 cm.
*Shape*.—Oblate.

Immature inflorescence:
*Diameter*.—2.3-2.7 cm.
*Color of ray florets, upper surface*.—RHS N81A.
*Lower surface*.—RHS N80B.

Mature inflorescence:
*Diameter*.—3.2-3.3 cm.
*Depth*.—1.0 cm.
*Total diameter of 'disc'*.—0.9 cm.
*Receptacle height*.—0.2 cm.
*Receptacle diameter*.—0.2 cm.

Ray florets:
*Average quantity of florets*.—About 45 in several whorls.
*Color of florets, upper surface*.—RHS N81A, maturing to RHS N81B.
*Lower surface*.—RHS N80B.
*Length*.—1.3-1.4 cm.
*Width*.—0.2-0.3 cm.
*Shape*.—Narrowly oblancelate.
*Apex shape*.—Praemorse.
*Margin*.—Entire.
*Texture, upper surface*.—Papillose.
*Lower surface*.—Papillose.

Disc florets:
*Average quantity of florets*.—About 100.
*Color of florets*.—RHS 2A maturing to RHS 5C with RHS 59B apex that itself fades to about RHS 48D.
*Length*.—0.4-0.45 cm.
*Width*.—0.1 cm.
*Shape*.—Tubular, elongated.
*Apex shape*.—Acute, 5 pointed.

Phyllaries:
*Quantity*.—20-25.
*Color, upper surface*.—RHS 137A.
*Lower surface*.—RHS 137C with RHS 137B margins.
*Length*.—0.9-1.3 cm.
*Width*.—0.2 cm.
*Shape*.—Ligulate.
*Apex shape*.—Acute.
*Based*.—Fused.
*Margins*.—Entire.
*Texture, upper surface*.—Glabrous.
*Lower surface*.—Smooth, glabrous.

Reproductive organs:
*Gynoecium*.—Present on both florets.
*Pistil*.—1.
*Length*.—0.5-0.7 cm.
*Style color*.—RHS 155B.
*Style length*.—0.4-0.6 cm.
*Stigma color*.—RHS 59A to RHS 59B.
*Stigma shape*.—Bi-parted.
*Ovary color*.—Not observed.
*Androecium*.—Not in good condition to observe.
*Fertility/seed set*.—Has not been observed on this hybrid.

Disease/pest resistance: Disease/pest resistance has not been observed on this hybrid.

What is claimed is:

1. A new and distinct variety of *Aster* plant named 'Synpin Henfirst' substantially as illustrated and described herein.

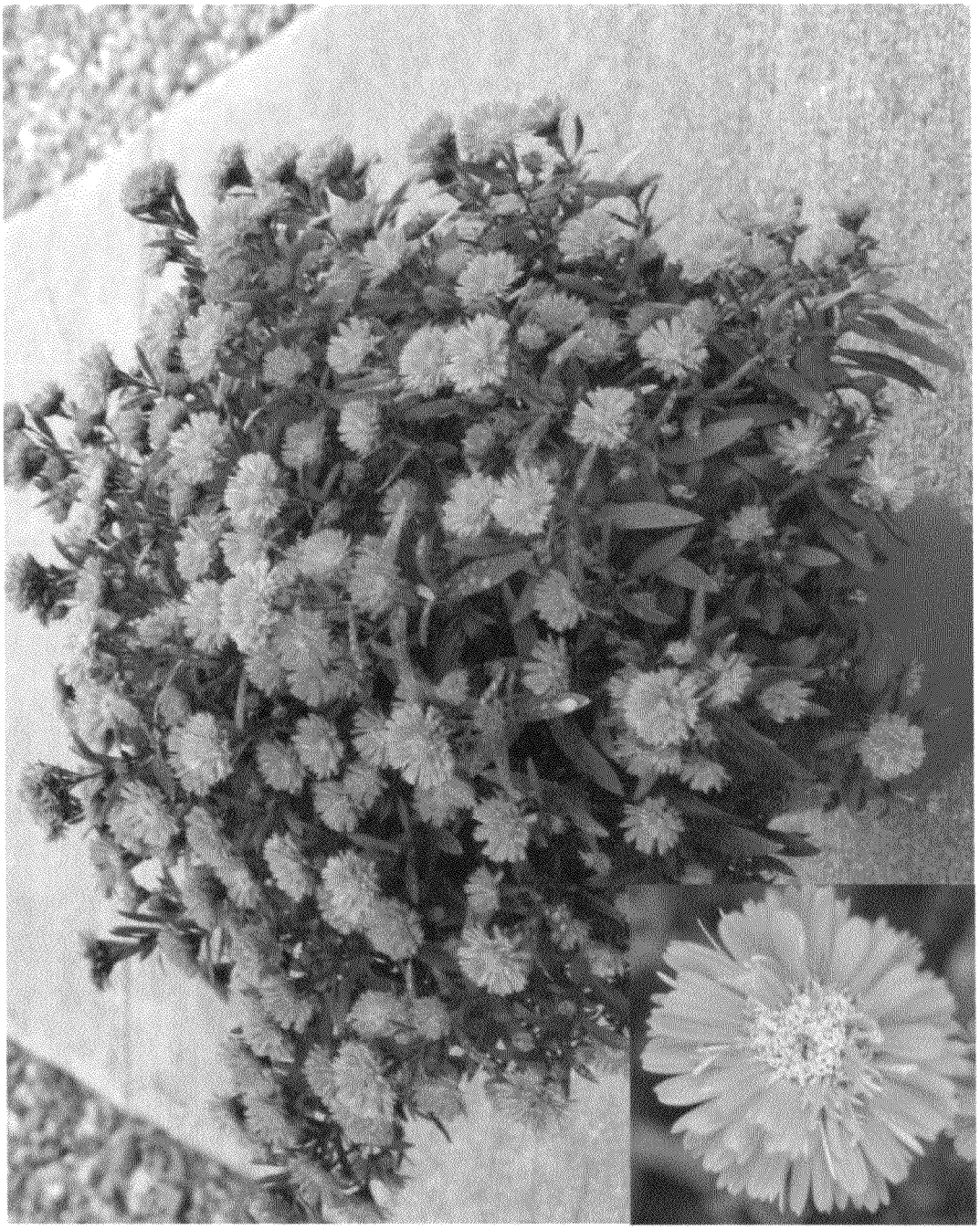

* * * * *